US00PP32669P3

(12) United States Plant Patent
Psenner

(10) Patent No.: US PP32,669 P3
(45) Date of Patent: Dec. 22, 2020

(54) ***EURYOPS* PLANT NAMED 'EUR16001'**

(50) Latin Name: *Euryops pectinatus*
Varietal Denomination: EUR16001

(71) Applicant: Thomas Psenner, Bozen (IT)

(72) Inventor: Thomas Psenner, Bozen (IT)

( * ) Notice: Subject to any disclaimer, the term of this patent is extended or adjusted under 35 U.S.C. 154(b) by 0 days.

(21) Appl. No.: 16/873,450

(22) Filed: Apr. 14, 2020

(65) Prior Publication Data

US 2020/0367399 P1 Nov. 19, 2020

(30) Foreign Application Priority Data

May 17, 2019 (CA) ..... PBR 19-9898

(51) Int. Cl.
*A01H 5/02* (2018.01)
*A01H 6/14* (2018.01)

(52) U.S. Cl.
USPC ..... Plt./226
CPC ..... *A01H 6/14* (2018.05)

(58) Field of Classification Search
USPC ..... Plt./263.1, 226
See application file for complete search history.

*Primary Examiner* — Susan McCormick Ewoldt
(74) *Attorney, Agent, or Firm* — C. Anne Whealy

(57) ABSTRACT

A new and distinct cultivar of *Euryops* plant named 'EUR16001', characterized by its compact, mounding and outwardly spreading plant habit; moderately vigorous growth habit; freely branching habit; dense and bushy appearance; freely flowering habit; long flowering period; large bright yellow-colored ray florets and darker yellow-colored disc florets; and good garden performance and drought resistance.

1 Drawing Sheet

Botanical designation: *Euryops pectinatus*.
Cultivar denomination: 'EUR16001'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9898. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Euryops* plant, botanically known as *Euryops pectinatus* and hereinafter referred to by the name 'EUR16001'.

The new *Euryops* plant is a product of a planned breeding program conducted by the Inventor in Bozen, Italy. The objective of the breeding program is to create compact and bushy *Euryops* plants with numerous large attractive flowers and good summer garden performance.

The new *Euryops* plant originated from a cross-pollination made by the Inventor in August, 2015 of an unnamed selection of *Euryops pectinatus*, not patented, as the female, or seed, parent with *Euryops pectinatus* 'Sonnenschein', not patented, as the male, or pollen, parent. The new *Euryops* plant was discovered and selected by the Inventor as a single flowering plant from within the progeny of the stated cross-pollination grown in a controlled greenhouse environment in Bozen, Italy in May, 2016.

Asexual reproduction of the *Euryops* plant by vegetative tip cuttings in Bozen, Italy since September, 2016 has shown that the unique features of this new *Euryops* plant are stable and reproduced true to type in successive generations.

SUMMARY OF THE INVENTION

Plants of the new *Euryops* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'EUR16001'. These characteristics in combination distinguish 'EUR16001' as a new and distinct *Euryops* plant:

1. Compact, mounding and outwardly spreading plant habit.
2. Moderately vigorous growth habit.
3. Freely branching habit; dense and bushy appearance.
4. Freely flowering habit.

5. Long flowering period.
6. Large bright yellow-colored ray florets and darker yellow-colored disc florets.
7. Good garden performance and drought resistance.

Plants of the new *Euryops* differ primarily from plants of the female parent selection in the following characteristics:

1. Plants of the new *Euryops* are more compact than and not as vigorous as plants of the female parent selection.
2. Plants of the new *Euryops* flower earlier than plants of the female parent selection.

Plants of the new *Euryops* differ primarily from plants of the male parent, 'Sonnenschein', in the following characteristics:

1. Plants of the new *Euryops* are more compact than and not as vigorous as plants of 'Sonnenschein'.
2. Plants of the new *Euryops* flower earlier than plants of 'Sonnenschein'.
3. Plants of the new *Euryops* have larger inflorescences than plants of 'Sonnenschein'.

Plants of the new *Euryops* can be compared to plants of *Euryops anthanasiae* 'Straesun', disclosed in U.S. Plant Pat. No. 18,373. In side-by-side comparisons, plants of the new *Euryops* differ primarily from plants of 'Straesun' in the following characteristics:

1. Plants of the new *Euryops* are more mounding than and not as upright as plants of 'Straesun'.
2. Plants of the new *Euryops* have larger inflorescences than plants of 'Straesun'.
3. Plants of the new *Euryops* have better summer garden performance than plants of 'Straesun'.

BRIEF DESCRIPTION OF THE PHOTOGRAPHS

The accompanying colored photographs illustrate the overall appearance of the new *Euryops* plant showing the colors as true as it is reasonably possible to obtain in colored reproductions of this type. Colors in the photographs may differ slightly from the color values cited in the detailed botanical description which accurately describe the colors of the new *Euryops* plant.

At the top of the photographic sheet (FIG. 1) is a side perspective view of a typical flowering plant of 'EUR16001' grown in a container and at the bottom of the photographic sheet is a close-up view of a typical flowering plant of 'EUR16001'.

DETAILED BOTANICAL DESCRIPTION

The aforementioned photographs and following observations and measurements describe plants grown during the summer in 15.25-cm containers in a polyethylene-covered greenhouse in St. Thomas, Ontario, Canada and under cultural practices typical of commercial *Euryops* production. During the production of the plants, day temperatures averaged 27° C. and night temperatures averaged 15° C. Plants were pinched when planted and were seven weeks from planting rooted cuttings when the photographs and description were taken. In the following description, color references are made to The Royal Horticultural Society Colour Chart, 2007 Edition, except where general terms of ordinary dictionary significance are used.

Botanical classification: *Euryops pectinatus* 'EUR16001'.

Parentage:

*Female parent*.—Unnamed selection of *Euryops pectinatus*, not patented.

*Male parent*.—*Euryops pectinatus* 'Sonnenschein', not patented.

Propagation:

*Type*.—Terminal vegetative cuttings.

*Time to initiate roots, summer*.—About ten days at ambient temperatures about from 17° C.

*Time to initiate roots, winter*.—About two weeks at ambient temperatures about 17° C.

*Time to produce a rooted young plant, summer*.—About three weeks at ambient temperatures about 17° C.

*Time to produce a rooted young plant, winter*.—About 25 days at ambient temperatures about 17° C.

*Root description*.—Fine, fleshy; typically white in color, actual color of the roots is dependent on substrate composition, water quality, fertilizers, substrate temperature and age of roots.

*Rooting habit*.—Freely branching; medium density.

Plant description:

*Plant and growth habit*.—Compact, mounding and outwardly spreading plant habit; inflorescences positioned above and beyond the foliar plane on strong peduncles; moderately vigorous growth habit and moderate growth rate.

*Plant height, soil level to top of foliar plane*.—About 25.8 cm.

*Plant height, soil level to top of floral plane*.—About 32 cm.

*Plant diameter*.—About 56 cm.

*Lateral branches*.—Quantity per plant: Freely branching habit with about two to three primary branches each with about six secondary branches. Length: About 6.4 cm. Diameter: About 4.6 mm. Internode length: About 1.2 cm. Strength: Strong. Aspect, primary branches: Erect to semi-upright. Aspect, secondary branches: About 45° from primary branch axis. Texture and luster: Smooth, glabrous; moderately glossy. Color, developing: Close to 144B. Color, developed: Close to 144A.

*Leaf description*.—Arrangement: Alternate, simple; sessile. Length: About 12.2 cm. Width: About 3.9 cm. Shape: Oblanceolate. Apex: Broadly acute with mucronate tip. Base: Clasping the stem. Margin: Deeply lobed, pinnately lobed to pinnatisect. Texture and luster, upper and lower surfaces: Smooth, glabrous; moderately glossy. Venation pattern: Pinnate. Color: Developing leaves, upper surface: Close to 137C. Developing leaves, lower surface: Close to 144A. Fully expanded leaves, upper surface: Close to N137A; venation, close to 138B. Fully expanded leaves, lower surface: Close to 147B; venation, close to 146A.

Inflorescence description:

*Appearance*.—Daisy-type inflorescence form with ligulate to oblanceolate-shaped ray florets; inflorescences terminal and axillary and positioned above and beyond the foliar plane on strong peduncles; disc and ray florets developing acropetally on a capitulum; inflorescences face mostly upright to outwardly.

*Flowering habit*.—Freely flowering habit with about 40 to 50 inflorescences developing per plant at one time.

*Fragrance*.—None detected.

*Flowering response*.—Plants of the new *Euryops* flower early and continuously from spring until frost; long flowering period; plants begin flowering about six weeks after planting.

*Inflorescence longevity*.—Inflorescences of plants of the new *Euryops* last about one to two weeks on the plant; inflorescences persistent.

*Inflorescence buds*.—Height: About 8 mm. Diameter: About 1 cm. Shape: Rounded. Texture and luster: Mostly smooth and glabrous; pubescence at the apex; matte. Color: Close to 144A.

*Inflorescence size*.—Diameter: Large, about 5.3 cm. Depth (height): About 1.5 cm. Disc diameter: About 1.5 cm to 1.7 cm.

*Ray florets*.—Quantity per inflorescence and arrangement: About 18 to 22 arranged in a single whorl. Length: About 2.4 cm. Width: About 6 mm. Shape: Ligulate to oblanceolate. Apex: Emarginate. Base: Obtuse. Margin: Entire, slightly undulate. Aspect: Mostly horizontal when fully developed and reflexing with development. Texture and luster, upper surface: Smooth, glabrous; matte. Texture and luster, lower surface: Longitudinally ridged, glabrous; matte. Color: When opening and fully opened, upper surface: Brighter than 9A; venation, close to 9A; color does not change with development. When opening and fully opened, lower surface: Brighter than 9A; venation, close to 9A; color does not change with development.

*Disc florets*.—Quantity per inflorescence and arrangement: About 122 spirally arranged in about eight whorls at the center of the receptacle. Length: About 4 mm to 6 mm. Diameter, apex: Less than 1 mm. Diameter, base: Less than 1 mm. Shape: Tubular; apex, five-pointed with acute points. Texture and luster, inner and outer surfaces: Smooth, glabrous; matte. Color, immature and mature: Close to 14A.

*Phyllaries*.—Quantity per inflorescence and arrangement: About 12 to 13 arranged in two whorls. Length: About 8 mm. Width: About 4 mm. Shape: Ovate. Apex: Acute. Base: Truncate. Margin: Entire. Texture and luster, upper surface: Mostly smooth, glabrous with pubescence at the apex; slightly glossy. Texture and luster, lower surface: Smooth, glabrous; matte. Color, upper and lower surfaces: Close to 144A.

*Peduncles*.—Length: About 18 cm. Diameter: About 1.4 mm. Strength: Strong. Aspect: About 30° to 45° from vertical. Texture and luster: Glabrous, slightly ribbed; matte. Color: Close to 146B.

*Reproductive organs*.—Androecium: Present on disc florets only. Quantity per floret: About five. Filament length: About 1 mm. Filament color: Close to 154D. Anther length: About 1 mm. Anther shape: Oblong. Anther color: Close to 13A. Pollen amount: If present, scarce. Pollen color: Close to 13A. Gynoecium: Present on both ray and disc florets. Pistil length: About 3.1 mm. Stigma diameter: Less than 1 mm. Stigma shape: Bi-parted. Stigma color: Close to 13A or 14A. Style length: About 3 mm. Style color: Close to 13A or 14A. Ovary color: Close to 154D.

*Seeds and fruits*.—To date, seed and fruit development has not been observed on plants of the new *Euryops*.

Pathogen & pest resistance: To date, plants of the new *Euryops* have not been shown to be resistant to pathogens and pests common to *Euryops* plants.

Garden performance: Plants of the new *Euryops* have been observed to have good summer garden performance and to tolerate rain, wind, tolerate drought conditions and tolerate temperatures ranging from 1° C. to 45° C.

It is claimed:

1. A new and distinct *Euryops* plant named 'EUR16001' as illustrated and described.

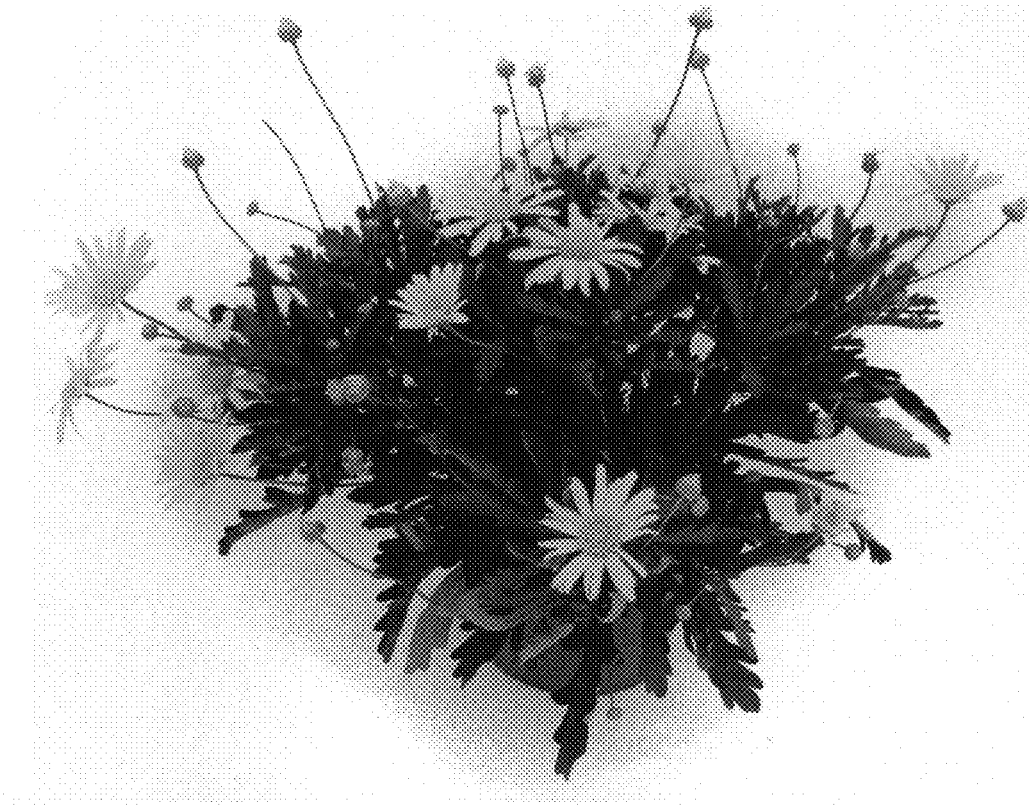
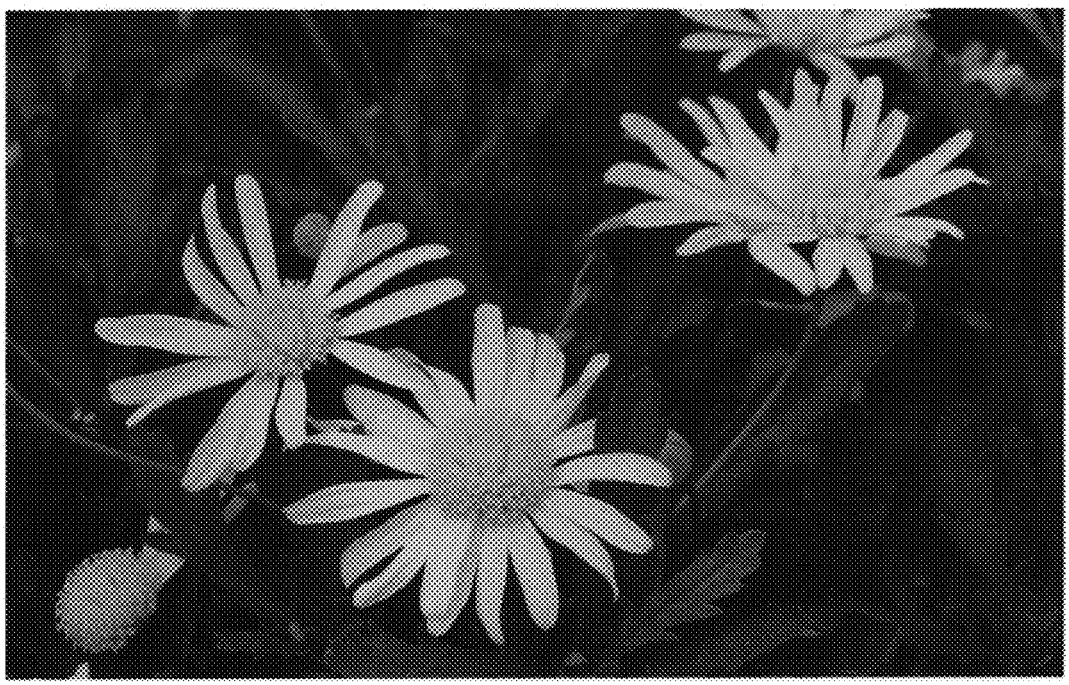

* * * * *